(12) United States Patent
Haisley

(10) Patent No.: US 8,417,310 B2
(45) Date of Patent: Apr. 9, 2013

(54) DIGITAL SWITCHING IN MULTI-SITE SENSOR

(75) Inventor: Charles Haisley, Boulder, CO (US)

(73) Assignee: Covidien LP, Mansfield, MA (US)

( * ) Notice: Subject to any disclaimer, the term of this patent is extended or adjusted under 35 U.S.C. 154(b) by 912 days.

(21) Appl. No.: 12/538,700

(22) Filed: Aug. 10, 2009

(65) Prior Publication Data

US 2011/0034789 A1 Feb. 10, 2011

(51) Int. Cl.
*A61B 5/1455* (2006.01)
(52) U.S. Cl. .......................... 600/344; 600/323
(58) Field of Classification Search .................. 600/310, 600/322, 323, 344
See application file for complete search history.

(56) References Cited

U.S. PATENT DOCUMENTS

| | | |
|---|---|---|
| 3,721,813 A | 3/1973 | Condon et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

U.S. Appl. No. 12/504,741, filed Jul. 17, 2009, Mannheimer, Paul D.

(Continued)

*Primary Examiner* — Eric Winakur
(74) *Attorney, Agent, or Firm* — Fletcher Yoder

(57) ABSTRACT

A system includes a flexible sensor configured to be placed into a first configuration and a second configuration, wherein the sensor is configured to measure a physiological characteristic. The sensor may include a first memory device configured to store a first set of calibration data and a second memory device configured to store a second set of calibration data. The system may further include a monitor coupled to the sensor, wherein the first memory device is accessible by the monitor in the first configuration and the second memory device is accessible by the monitor in the second configuration.

20 Claims, 5 Drawing Sheets

U.S. PATENT DOCUMENTS

| | | | |
|---|---|---|---|
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hausman et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,539 A | 8/1991 | Schmitt et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,084,327 A | 1/1992 | Stengel | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,273,036 A | 12/1993 | Kronberg et al. | |
| 5,275,159 A | 1/1994 | Griebel | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |
| 5,385,143 A | 1/1995 | Aoyagi | |
| 5,387,122 A | 2/1995 | Goldberger et al. | |
| 5,390,670 A | 2/1995 | Centa et al. | |
| 5,392,777 A | 2/1995 | Swedlow et al. | |
| 5,398,680 A | 3/1995 | Polson et al. | |
| 5,402,777 A | 4/1995 | Warring et al. | |
| 5,411,023 A | 5/1995 | Morris, Sr. et al. | |
| 5,411,024 A | 5/1995 | Thomas et al. | |
| 5,413,099 A | 5/1995 | Schmidt et al. | |
| 5,413,100 A | 5/1995 | Barthelemy et al. | |
| 5,413,101 A | 5/1995 | Sugiura | |
| 5,413,102 A | 5/1995 | Schmidt et al. | |
| 5,417,207 A | 5/1995 | Young et al. | |
| 5,421,329 A | 6/1995 | Casciani et al. | |
| 5,425,360 A | 6/1995 | Nelson | |
| 5,425,362 A | 6/1995 | Siker et al. | |
| 5,427,093 A | 6/1995 | Ogawa et al. | |
| 5,429,128 A | 7/1995 | Cadell et al. | |
| 5,429,129 A | 7/1995 | Lovejoy et al. | |
| 5,431,159 A | 7/1995 | Baker et al. | |
| 5,431,170 A | 7/1995 | Mathews | |
| 5,437,275 A | 8/1995 | Amundsen et al. | |
| 5,438,986 A | 8/1995 | Disch et al. | |
| 5,448,991 A | 9/1995 | Polson et al. | |
| 5,452,717 A | 9/1995 | Branigan et al. | |
| 5,465,714 A | 11/1995 | Scheuing | |

| | | | | | |
|---|---|---|---|---|---|
| 5,469,845 A | 11/1995 | DeLonzor et al. | 5,746,206 A | 5/1998 | Mannheimer |
| RE35,122 E | 12/1995 | Corenman et al. | 5,746,697 A | 5/1998 | Swedlow et al. |
| 5,474,065 A | 12/1995 | Meathrel et al. | 5,752,914 A | 5/1998 | DeLonzor et al. |
| 5,482,034 A | 1/1996 | Lewis et al. | 5,755,226 A | 5/1998 | Carim et al. |
| 5,482,036 A | 1/1996 | Diab et al. | 5,758,644 A | 6/1998 | Diab et al. |
| 5,483,646 A | 1/1996 | Uchikoga | 5,760,910 A | 6/1998 | Lepper, Jr. et al. |
| 5,485,847 A | 1/1996 | Baker, Jr. | 5,766,125 A | 6/1998 | Aoyagi et al. |
| 5,490,505 A | 2/1996 | Diab et al. | 5,766,127 A | 6/1998 | Pologe et al. |
| 5,490,523 A | 2/1996 | Isaacson et al. | 5,769,785 A | 6/1998 | Diab et al. |
| 5,491,299 A | 2/1996 | Naylor et al. | 5,772,587 A | 6/1998 | Gratton et al. |
| 5,494,032 A | 2/1996 | Robinson et al. | 5,774,213 A | 6/1998 | Trebino et al. |
| 5,497,771 A | 3/1996 | Rosenheimer | 5,776,058 A | 7/1998 | Levinson et al. |
| 5,499,627 A | 3/1996 | Steuer et al. | 5,776,059 A | 7/1998 | Kaestle |
| 5,503,148 A | 4/1996 | Pologe et al. | 5,779,630 A | 7/1998 | Fein et al. |
| 5,505,199 A | 4/1996 | Kim | 5,779,631 A | 7/1998 | Chance |
| 5,507,286 A | 4/1996 | Solenberger | 5,782,237 A | 7/1998 | Casciani et al. |
| 5,511,546 A | 4/1996 | Hon | 5,782,756 A | 7/1998 | Mannheimer |
| 5,517,988 A | 5/1996 | Gerhard | 5,782,757 A | 7/1998 | Diab et al. |
| 5,520,177 A | 5/1996 | Ogawa et al. | 5,782,758 A | 7/1998 | Ausec et al. |
| 5,521,851 A | 5/1996 | Wei et al. | 5,786,592 A | 7/1998 | Hök |
| 5,522,388 A | 6/1996 | Ishikawa et al. | 5,790,729 A | 8/1998 | Pologe et al. |
| 5,524,617 A | 6/1996 | Mannheimer | 5,792,052 A | 8/1998 | Isaacson et al. |
| 5,529,064 A | 6/1996 | Rall et al. | 5,795,292 A | 8/1998 | Lewis et al. |
| 5,533,507 A | 7/1996 | Potratz et al. | 5,797,841 A | 8/1998 | DeLonzor et al. |
| 5,551,423 A | 9/1996 | Sugiura | 5,800,348 A | 9/1998 | Kaestle |
| 5,551,424 A | 9/1996 | Morrison et al. | 5,800,349 A | 9/1998 | Isaacson et al. |
| 5,553,614 A | 9/1996 | Chance | 5,803,910 A | 9/1998 | Potratz |
| 5,553,615 A | 9/1996 | Carim et al. | 5,807,246 A | 9/1998 | Sakaguchi et al. |
| 5,555,882 A | 9/1996 | Richardson et al. | 5,807,247 A | 9/1998 | Merchant et al. |
| 5,558,096 A | 9/1996 | Palatnik | 5,807,248 A | 9/1998 | Mills |
| 5,560,355 A | 10/1996 | Merchant et al. | 5,810,723 A | 9/1998 | Aldrich |
| 5,564,417 A | 10/1996 | Chance | 5,810,724 A | 9/1998 | Gronvall |
| 5,575,284 A | 11/1996 | Athan et al. | 5,813,980 A | 9/1998 | Levinson et al. |
| 5,575,285 A | 11/1996 | Takanashi et al. | 5,817,008 A | 10/1998 | Rafert et al. |
| 5,577,500 A | 11/1996 | Potratz | 5,817,009 A | 10/1998 | Rosenheimer et al. |
| 5,582,169 A | 12/1996 | Oda et al. | 5,817,010 A | 10/1998 | Hibl |
| 5,584,296 A | 12/1996 | Cui et al. | 5,818,985 A | 10/1998 | Merchant et al. |
| 5,588,425 A | 12/1996 | Sackner et al. | 5,820,550 A | 10/1998 | Polson et al. |
| 5,588,427 A | 12/1996 | Tien | 5,823,950 A | 10/1998 | Diab et al. |
| 5,590,652 A | 1/1997 | Inai | 5,823,952 A | 10/1998 | Levinson et al. |
| 5,595,176 A | 1/1997 | Yamaura | 5,827,182 A | 10/1998 | Raley et al. |
| 5,596,986 A | 1/1997 | Goldfarb | 5,830,135 A | 11/1998 | Bosque et al. |
| 5,611,337 A | 3/1997 | Bukta | 5,830,136 A | 11/1998 | DeLonzor et al. |
| 5,617,852 A | 4/1997 | MacGregor | 5,830,137 A | 11/1998 | Scharf |
| 5,619,992 A | 4/1997 | Guthrie et al. | 5,839,439 A | 11/1998 | Nierlich et al. |
| 5,626,140 A | 5/1997 | Feldman et al. | RE36,000 E | 12/1998 | Swedlow et al. |
| 5,630,413 A | 5/1997 | Thomas et al. | 5,842,979 A | 12/1998 | Jarman et al. |
| 5,632,272 A | 5/1997 | Diab et al. | 5,842,981 A | 12/1998 | Larsen et al. |
| 5,632,273 A | 5/1997 | Suzuki | 5,842,982 A | 12/1998 | Mannheimer |
| 5,634,459 A | 6/1997 | Gardosi | 5,846,190 A | 12/1998 | Woehrle |
| 5,638,593 A | 6/1997 | Gerhardt et al. | 5,851,178 A | 12/1998 | Aronow |
| 5,638,818 A | 6/1997 | Diab et al. | 5,851,179 A | 12/1998 | Ritson et al. |
| 5,645,060 A | 7/1997 | Yorkey et al. | 5,853,364 A | 12/1998 | Baker, Jr. et al. |
| 5,645,440 A | 7/1997 | Tobler et al. | 5,860,919 A | 1/1999 | Kiani-Azarbayjany et al. |
| 5,660,567 A | 8/1997 | Nierlich et al. | 5,865,736 A | 2/1999 | Baker, Jr. et al. |
| 5,662,105 A | 9/1997 | Tien | 5,871,442 A | 2/1999 | Madarasz et al. |
| 5,662,106 A | 9/1997 | Swedlow et al. | 5,879,294 A | 3/1999 | Anderson et al. |
| 5,666,952 A | 9/1997 | Fuse et al. | 5,885,213 A | 3/1999 | Richardson et al. |
| 5,671,529 A | 9/1997 | Nelson | 5,890,929 A | 4/1999 | Mills et al. |
| 5,673,692 A | 10/1997 | Schulze et al. | 5,891,021 A | 4/1999 | Dillon et al. |
| 5,673,693 A | 10/1997 | Solenberger | 5,891,022 A | 4/1999 | Pologe |
| 5,676,139 A | 10/1997 | Goldberger et al. | 5,891,024 A | 4/1999 | Jarman et al. |
| 5,676,141 A | 10/1997 | Hollub | 5,891,025 A | 4/1999 | Buschmann et al. |
| 5,678,544 A | 10/1997 | DeLonzor et al. | 5,891,026 A | 4/1999 | Wang et al. |
| 5,680,857 A | 10/1997 | Pelikan et al. | 5,902,235 A | 5/1999 | Lewis et al. |
| 5,685,299 A | 11/1997 | Diab et al. | 5,910,108 A | 6/1999 | Solenberger |
| 5,685,301 A | 11/1997 | Klomhaus | 5,911,690 A | 6/1999 | Rall |
| 5,687,719 A | 11/1997 | Sato et al. | 5,912,656 A | 6/1999 | Tham et al. |
| 5,687,722 A | 11/1997 | Tien et al. | 5,913,819 A | 6/1999 | Taylor et al. |
| 5,692,503 A | 12/1997 | Kuenstner | 5,916,154 A | 6/1999 | Hobbs et al. |
| 5,692,505 A | 12/1997 | Fouts | 5,916,155 A | 6/1999 | Levinson et al. |
| 5,709,205 A | 1/1998 | Bukta | 5,919,133 A | 7/1999 | Taylor et al. |
| 5,713,355 A | 2/1998 | Richardson et al. | 5,919,134 A | 7/1999 | Diab |
| 5,724,967 A | 3/1998 | Venkatachalam | 5,920,263 A | 7/1999 | Huttenhoff et al. |
| 5,727,547 A | 3/1998 | Levinson et al. | 5,921,921 A | 7/1999 | Potratz et al. |
| 5,731,582 A | 3/1998 | West | 5,922,607 A | 7/1999 | Bernreuter |
| D393,830 S | 4/1998 | Tobler et al. | 5,924,979 A | 7/1999 | Swedlow et al. |
| 5,743,260 A | 4/1998 | Chung et al. | 5,924,980 A | 7/1999 | Coetzee |
| 5,743,263 A | 4/1998 | Baker, Jr. | 5,924,982 A | 7/1999 | Chin |

| | | | | | | |
|---|---|---|---|---|---|---|
| 5,924,985 | A | 7/1999 | Jones | 6,198,951 | B1 | 3/2001 | Kosuda et al. |
| 5,934,277 | A | 8/1999 | Mortz | 6,206,830 | B1 | 3/2001 | Diab et al. |
| 5,934,925 | A | 8/1999 | Tobler et al. | 6,213,952 | B1 | 4/2001 | Finarov et al. |
| 5,940,182 | A | 8/1999 | Lepper, Jr. et al. | 6,217,523 | B1 | 4/2001 | Amano et al. |
| 5,954,644 | A | 9/1999 | Dettling et al. | 6,222,189 | B1 | 4/2001 | Misner et al. |
| 5,960,610 | A | 10/1999 | Levinson et al. | 6,226,539 | B1 | 5/2001 | Potratz |
| 5,961,450 | A | 10/1999 | Merchant et al. | 6,226,540 | B1 | 5/2001 | Bernreuter et al. |
| 5,961,452 | A | 10/1999 | Chung et al. | 6,229,856 | B1 | 5/2001 | Diab et al. |
| 5,964,701 | A | 10/1999 | Asada et al. | 6,230,035 | B1 | 5/2001 | Aoyagi et al. |
| 5,971,930 | A | 10/1999 | Elghazzawi | 6,233,470 | B1 | 5/2001 | Tsuchiya |
| 5,978,691 | A | 11/1999 | Mills | 6,236,871 | B1 | 5/2001 | Tsuchiya |
| 5,978,693 | A | 11/1999 | Hamilton et al. | 6,236,872 | B1 | 5/2001 | Diab et al. |
| 5,983,122 | A | 11/1999 | Jarman et al. | 6,240,305 | B1 | 5/2001 | Tsuchiya |
| 5,987,343 | A | 11/1999 | Kinast | 6,253,097 | B1 | 6/2001 | Aronow et al. |
| 5,991,648 | A | 11/1999 | Levin | 6,253,098 | B1 | 6/2001 | Walker et al. |
| 5,995,855 | A | 11/1999 | Kiani et al. | 6,256,523 | B1 | 7/2001 | Diab et al. |
| 5,995,856 | A | 11/1999 | Mannheimer et al. | 6,256,524 | B1 | 7/2001 | Walker et al. |
| 5,995,858 | A | 11/1999 | Kinast | 6,261,236 | B1 | 7/2001 | Grimblatov |
| 5,995,859 | A | 11/1999 | Takahashi | 6,263,221 | B1 | 7/2001 | Chance et al. |
| 5,997,343 | A | 12/1999 | Mills et al. | 6,263,222 | B1 | 7/2001 | Diab et al. |
| 5,999,834 | A | 12/1999 | Wang et al. | 6,263,223 | B1 | 7/2001 | Shepherd et al. |
| 6,002,952 | A | 12/1999 | Diab et al. | 6,266,546 | B1 | 7/2001 | Steuer et al. |
| 6,005,658 | A | 12/1999 | Kaluza et al. | 6,266,547 | B1 | 7/2001 | Walker et al. |
| 6,006,120 | A | 12/1999 | Levin | 6,272,363 | B1 | 8/2001 | Casciani et al. |
| 6,011,985 | A | 1/2000 | Athan et al. | 6,278,522 | B1 | 8/2001 | Lepper, Jr. et al. |
| 6,011,986 | A | 1/2000 | Diab et al. | 6,280,213 | B1 | 8/2001 | Tobler et al. |
| 6,014,576 | A | 1/2000 | Raley et al. | 6,280,381 | B1 | 8/2001 | Malin et al. |
| 6,018,673 | A | 1/2000 | Chin et al. | 6,285,894 | B1 | 9/2001 | Oppelt et al. |
| 6,018,674 | A | 1/2000 | Aronow | 6,285,895 | B1 | 9/2001 | Ristolainen et al. |
| 6,022,321 | A | 2/2000 | Amano et al. | 6,285,896 | B1 | 9/2001 | Tobler et al. |
| 6,023,541 | A | 2/2000 | Merchant et al. | 6,298,252 | B1 | 10/2001 | Kovach et al. |
| 6,026,312 | A | 2/2000 | Shemwell et al. | 6,308,089 | B1 | 10/2001 | von der Ruhr et al. |
| 6,026,314 | A | 2/2000 | Amerov et al. | 6,321,100 | B1 | 11/2001 | Parker |
| 6,031,603 | A | 2/2000 | Fine et al. | 6,330,468 | B1 | 12/2001 | Scharf |
| 6,035,223 | A | 3/2000 | Baker, Jr. | 6,334,065 | B1 | 12/2001 | Al-Ali et al. |
| 6,036,642 | A | 3/2000 | Diab et al. | 6,339,715 | B1 | 1/2002 | Bahr et al. |
| 6,041,247 | A | 3/2000 | Weckstrom et al. | 6,343,223 | B1 | 1/2002 | Chin et al. |
| 6,044,283 | A | 3/2000 | Fein et al. | 6,343,224 | B1 | 1/2002 | Parker |
| 6,047,201 | A | 4/2000 | Jackson, III | 6,349,228 | B1 | 2/2002 | Kiani et al. |
| 6,061,584 | A | 5/2000 | Lovejoy et al. | 6,351,658 | B1 | 2/2002 | Middleman et al. |
| 6,064,898 | A | 5/2000 | Aldrich | 6,353,569 | B1 * | 3/2002 | Mizuno et al. ............. 365/210.1 |
| 6,064,899 | A | 5/2000 | Fein et al. | 6,353,750 | B1 | 3/2002 | Kimura et al. |
| 6,067,462 | A | 5/2000 | Diab et al. | 6,356,774 | B1 | 3/2002 | Bernstein et al. |
| 6,073,038 | A | 6/2000 | Wang et al. | 6,360,113 | B1 | 3/2002 | Dettling |
| 6,078,833 | A | 6/2000 | Hueber | 6,360,114 | B1 | 3/2002 | Diab et al. |
| 6,081,735 | A | 6/2000 | Diab et al. | 6,361,501 | B1 | 3/2002 | Amano et al. |
| 6,081,742 | A | 6/2000 | Amano et al. | 6,363,269 | B1 | 3/2002 | Hanna et al. |
| 6,083,157 | A | 7/2000 | Noller | 6,370,408 | B1 | 4/2002 | Merchant et al. |
| 6,083,172 | A | 7/2000 | Baker, Jr. et al. | 6,370,409 | B1 | 4/2002 | Chung et al. |
| 6,088,607 | A | 7/2000 | Diab et al. | 6,374,129 | B1 | 4/2002 | Chin et al. |
| 6,094,592 | A | 7/2000 | Yorkey et al. | 6,377,829 | B1 | 4/2002 | Al-Ali et al. |
| 6,095,974 | A | 8/2000 | Shemwell et al. | 6,381,479 | B1 | 4/2002 | Norris |
| 6,104,938 | A | 8/2000 | Huiku et al. | 6,381,480 | B1 | 4/2002 | Stoddart et al. |
| 6,112,107 | A | 8/2000 | Hannula | 6,385,471 | B1 | 5/2002 | Mortz |
| 6,113,541 | A | 9/2000 | Dias et al. | 6,385,821 | B1 | 5/2002 | Modgil et al. |
| 6,115,621 | A | 9/2000 | Chin | 6,388,240 | B2 | 5/2002 | Schulz et al. |
| 6,122,535 | A | 9/2000 | Kaestle et al. | 6,393,310 | B1 | 5/2002 | Kuenster |
| 6,133,994 | A | 10/2000 | Mathews et al. | 6,397,091 | B2 | 5/2002 | Diab et al. |
| 6,135,952 | A | 10/2000 | Coetzee | 6,397,092 | B1 | 5/2002 | Norris et al. |
| 6,144,444 | A | 11/2000 | Haworth et al. | 6,397,093 | B1 | 5/2002 | Aldrich |
| 6,144,867 | A | 11/2000 | Walker et al. | 6,400,971 | B1 | 6/2002 | Finarov et al. |
| 6,144,868 | A | 11/2000 | Parker | 6,400,972 | B1 | 6/2002 | Fine |
| 6,149,481 | A | 11/2000 | Wang et al. | 6,402,690 | B1 | 6/2002 | Rhee et al. |
| 6,150,951 | A | 11/2000 | Olejniczak | 6,408,198 | B1 | 6/2002 | Hanna et al. |
| 6,151,107 | A | 11/2000 | Schöllermann et al. | 6,411,832 | B1 | 6/2002 | Guthermann |
| 6,151,518 | A | 11/2000 | Hayashi | 6,411,833 | B1 | 6/2002 | Baker, Jr. et al. |
| 6,152,754 | A | 11/2000 | Gerhardt et al. | 6,419,671 | B1 | 7/2002 | Lemberg |
| 6,154,667 | A | 11/2000 | Miura et al. | 6,421,549 | B1 | 7/2002 | Jacques |
| 6,157,850 | A | 12/2000 | Diab et al. | 6,430,423 | B2 | 8/2002 | DeLonzor et al. |
| 6,163,715 | A | 12/2000 | Larsen et al. | 6,430,513 | B1 | 8/2002 | Wang et al. |
| 6,165,005 | A | 12/2000 | Mills et al. | 6,430,525 | B1 | 8/2002 | Weber et al. |
| 6,173,196 | B1 | 1/2001 | Delonzor et al. | 6,434,408 | B1 | 8/2002 | Heckel et al. |
| 6,178,343 | B1 | 1/2001 | Bindszus et al. | 6,438,399 | B1 | 8/2002 | Kurth |
| 6,181,958 | B1 | 1/2001 | Steuer et al. | 6,449,501 | B1 | 9/2002 | Reuss |
| 6,181,959 | B1 | 1/2001 | Schöllermann et al. | 6,453,183 | B1 | 9/2002 | Walker |
| 6,184,521 | B1 | 2/2001 | Coffin, IV et al. | 6,453,184 | B1 | 9/2002 | Hyogo et al. |
| 6,188,470 | B1 | 2/2001 | Grace | 6,456,862 | B2 | 9/2002 | Benni |
| 6,192,260 | B1 | 2/2001 | Chance | 6,461,305 | B1 | 10/2002 | Schnall |
| 6,195,575 | B1 | 2/2001 | Levinson | 6,463,310 | B1 | 10/2002 | Swedlow et al. |

| | | |
|---|---|---|
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B1 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Terry et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |

| | | |
|---|---|---|
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,048,687 B1 | 5/2006 | Reuss et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Achilefu et al. |
| 7,209,775 B2 | 4/2007 | Bae et al. |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,425 B2 | 9/2007 | Al-Ali |
| 7,272,426 B2 | 9/2007 | Scmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,371,981 B2 | 5/2008 | Abdul-Hafiz |
| 7,392,074 B2 | 6/2008 | Isaacson et al. |
| 7,428,432 B2 | 9/2008 | Ali et al. |
| 7,438,683 B2 | 10/2008 | Al-Ali et al. |
| 2001/0021803 A1 | 9/2001 | Blank et al. |
| 2001/0051767 A1 | 12/2001 | Williams et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boaz et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |

| | | |
|---|---|---|
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0020887 A1 | 1/2005 | Goldberg |
| 2005/0020894 A1 | 1/2005 | Norris et al. |
| 2005/0033128 A1 | 2/2005 | Ali et al. |
| 2005/0033129 A1 | 2/2005 | Edgar, Jr. et al. |
| 2005/0043599 A1 | 2/2005 | O'Mara |
| 2005/0043600 A1 | 2/2005 | Diab et al. |
| 2005/0049470 A1 | 3/2005 | Terry |
| 2005/0049471 A1 | 3/2005 | Aceti |
| 2005/0065417 A1 | 3/2005 | Ali et al. |
| 2005/0075550 A1 | 4/2005 | Lindekugel |
| 2005/0101848 A1 | 5/2005 | Al-Ali et al. |
| 2005/0113651 A1 | 5/2005 | Wood et al. |
| 2005/0177034 A1 | 8/2005 | Beaumont |
| 2005/0192488 A1 | 9/2005 | Bryenton et al. |
| 2005/0197548 A1 | 9/2005 | Dietiker |
| 2005/0228248 A1 | 10/2005 | Dietiker |
| 2005/0277819 A1 | 12/2005 | Kiani et al. |
| 2005/0283059 A1 | 12/2005 | Iyer et al. |
| 2006/0025660 A1 | 2/2006 | Swedlow et al. |
| 2006/0030762 A1 | 2/2006 | David et al. |
| 2006/0030763 A1 | 2/2006 | Mannheimer et al. |
| 2006/0030764 A1 | 2/2006 | Porges et al. |
| 2006/0030765 A1 | 2/2006 | Swedlow et al. |
| 2006/0058594 A1 | 3/2006 | Ishizuka et al. |
| 2006/0084852 A1 | 4/2006 | Mason et al. |
| 2006/0089547 A1 | 4/2006 | Sarussi |
| 2006/0106294 A1 | 5/2006 | Maser et al. |
| 2006/0161054 A1 | 7/2006 | Reuss et al. |
| 2006/0195028 A1 | 8/2006 | Hannula et al. |
| 2006/0200018 A1 | 9/2006 | Al-Ali |
| 2006/0211925 A1 | 9/2006 | Lamego et al. |
| 2006/0211932 A1 | 9/2006 | Al-Ali et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224058 A1 | 10/2006 | Mannheimer |
| 2006/0229510 A1 | 10/2006 | Fein et al. |
| 2006/0229511 A1 | 10/2006 | Fein et al. |
| 2006/0247501 A1 | 11/2006 | Ali |
| 2006/0258921 A1 | 11/2006 | Addison et al. |
| 2006/0258926 A1 | 11/2006 | Ali et al. |
| 2006/0276700 A1 | 12/2006 | O'Neil et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0043269 A1 | 2/2007 | Mannheimer et al. |
| 2007/0043270 A1 | 2/2007 | Mannheimer et al. |
| 2007/0043271 A1 | 2/2007 | Mannheimer et al. |
| 2007/0043272 A1 | 2/2007 | Mannheimer et al. |
| 2007/0043273 A1 | 2/2007 | Mannheimer et al. |
| 2007/0043274 A1 | 2/2007 | Mannheimer et al. |
| 2007/0043275 A1 | 2/2007 | Mannheimer et al. |
| 2007/0043276 A1 | 2/2007 | Mannheimer et al. |
| 2007/0043277 A1 | 2/2007 | Mannheimer et al. |
| 2007/0043278 A1 | 2/2007 | Mannheimer et al. |
| 2007/0043279 A1 | 2/2007 | Mannheimer et al. |
| 2007/0043280 A1 | 2/2007 | Mannheimer et al. |
| 2007/0043282 A1 | 2/2007 | Mannheimer et al. |
| 2007/0073116 A1 | 3/2007 | Kiani et al. |
| 2007/0073121 A1 | 3/2007 | Hoarau et al. |
| 2007/0073125 A1 | 3/2007 | Hoarau et al. |
| 2007/0073126 A1 | 3/2007 | Raridan, Jr. |
| 2007/0073127 A1 | 3/2007 | Kiani et al. |
| 2007/0073128 A1 | 3/2007 | Hoarau et al. |
| 2007/0088207 A1 | 4/2007 | Mannheimer et al. |
| 2007/0100220 A1 | 5/2007 | Baker, Jr. |
| 2007/0123756 A1 | 5/2007 | Kitajima et al. |
| 2007/0244376 A1 | 10/2007 | Wang |
| 2008/0039701 A1 | 2/2008 | Ali et al. |
| 2008/0081969 A1 | 4/2008 | Feldman et al. |
| 2008/0081970 A1 | 4/2008 | Boyce et al. |
| 2008/0088467 A1 | 4/2008 | Al-Ali |
| 2008/0221413 A1 | 9/2008 | Hoarau |
| 2008/0221462 A1 | 9/2008 | Baker |
| 2008/0287757 A1 | 11/2008 | Berson et al. |
| 2011/0015507 A1* | 1/2011 | Mannheimer .................. 600/324 |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0531631 | 3/1993 |
| EP | 0724860 | 8/1996 |
| FR | 2685865 | 7/1993 |
| JP | 2111343 | 4/1990 |
| JP | 5049625 | 3/1993 |
| JP | 6014906 | 1/1994 |
| JP | 6269430 | 9/1994 |
| JP | 7236625 | 9/1995 |
| JP | 2000237170 | 9/2000 |
| JP | 2003275192 | 9/2003 |
| JP | 2004089546 | 3/2004 |
| JP | 2004159810 | 6/2004 |
| JP | 2004329406 | 11/2004 |
| JP | 2004337605 | 12/2004 |
| JP | 2004344367 | 12/2004 |
| JP | 2004351107 | 12/2004 |
| JP | 2007020836 | 2/2007 |
| JP | 2007117641 | 5/2007 |
| JP | 2007190122 | 8/2007 |
| WO | WO8909566 | 10/1989 |
| WO | WO9001293 | 2/1990 |
| WO | WO9111137 | 8/1991 |
| WO | WO9316629 | 9/1993 |
| WO | WO9502358 | 1/1995 |
| WO | WO9736536 | 10/1997 |
| WO | WO9857577 | 12/1998 |
| WO | WO9947039 | 9/1999 |
| WO | WO0059374 | 10/2000 |
| WO | WO03011127 | 2/2003 |
| WO | WO2005010567 | 2/2005 |
| WO | WO2005010568 | 2/2005 |

OTHER PUBLICATIONS

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

DeKock, Marc; "Pulse Oximetry Probe Adhesive Disks: a Potential for Infant Aspiration," *Anesthesiology*, vol. 89, pp. 1603-1604 (1998).

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Irie, A., et al.; "Respiration Monitors—Pulse Oximeters," *Neonatal Care*, vol. 15, No. 12, pp. 78-83 (2002) (Article in Japanese—contains English summary of article).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Bentley, David J. et al.; "Measure Pressure with Thin Film"; Paper Film & Foil Converter; May 1, 2003.

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

\* cited by examiner

DIGITAL SWITCHING IN MULTI-SITE SENSOR

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed and/or scattered. More specifically, the light passed through the tissue is typically selected to be of one or more wavelengths that may be absorbed and/or scattered by the blood in an amount correlative to the amount of the blood constituent present in the blood. The amount of light absorbed and/or scattered may then be used to estimate the amount of blood constituent in the tissue using various algorithms. This determination may be performed in a monitor coupled to the sensor that receives the necessary data for the blood constituent calculation.

Some sensors may be capable of application to multiple placement sites on a patient's body. For example, sensors may be placed on a patient's forehead, a patient's digit, etc. To determine the amount of constituent based on the sensor data, the monitor coupled to the sensor may use specific algorithms or calibration coefficients for each placement site and sensor configuration. However, the monitor should recognize (have) the correct site on which the sensor is being placed to properly calculate physiological characteristics of the patient. Accordingly, if the user of the sensor incorrectly notifies (or does not notify) the monitor of the configuration of the sensor, incorrect data may be obtained when physiological measurements are made by the pulse oximeter.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to non-invasively measuring physiologic parameters corresponding to blood flow in a patient by emitting light into a patient's tissue with light emitters (e.g., light emitting diodes) and photoelectrically detecting the light after it has passed through the patient's tissue. More specifically, present embodiments are directed to automatically allowing a pulse oximetry monitor to receive sensor coefficients from a flexible type pulse oximetry sensor. The sensor may be deformable such that the sensor may be used on multiple sensor sites on a patient. For example, the sensor may be curved to be placed on a digit of a patient or it may be straightened for use on the forehead of a patient. The sensor may include a separate memory corresponding to each of these configurations. Alternatively, the sensor may include one or more resistors, for example, whose values correspond to the actual wavelengths and to coefficients used in algorithms for computing the physiological parameters. Based on a switch, which may be implemented via contacts in the sensor, the monitor may be coupled to the memory (or resistors) that include coefficients related to the current configuration of the sensor. The monitor may read the coefficients from the activated memory (or resistor) to allow for proper decoding of physiological parameters of a patient.

Figure 1:
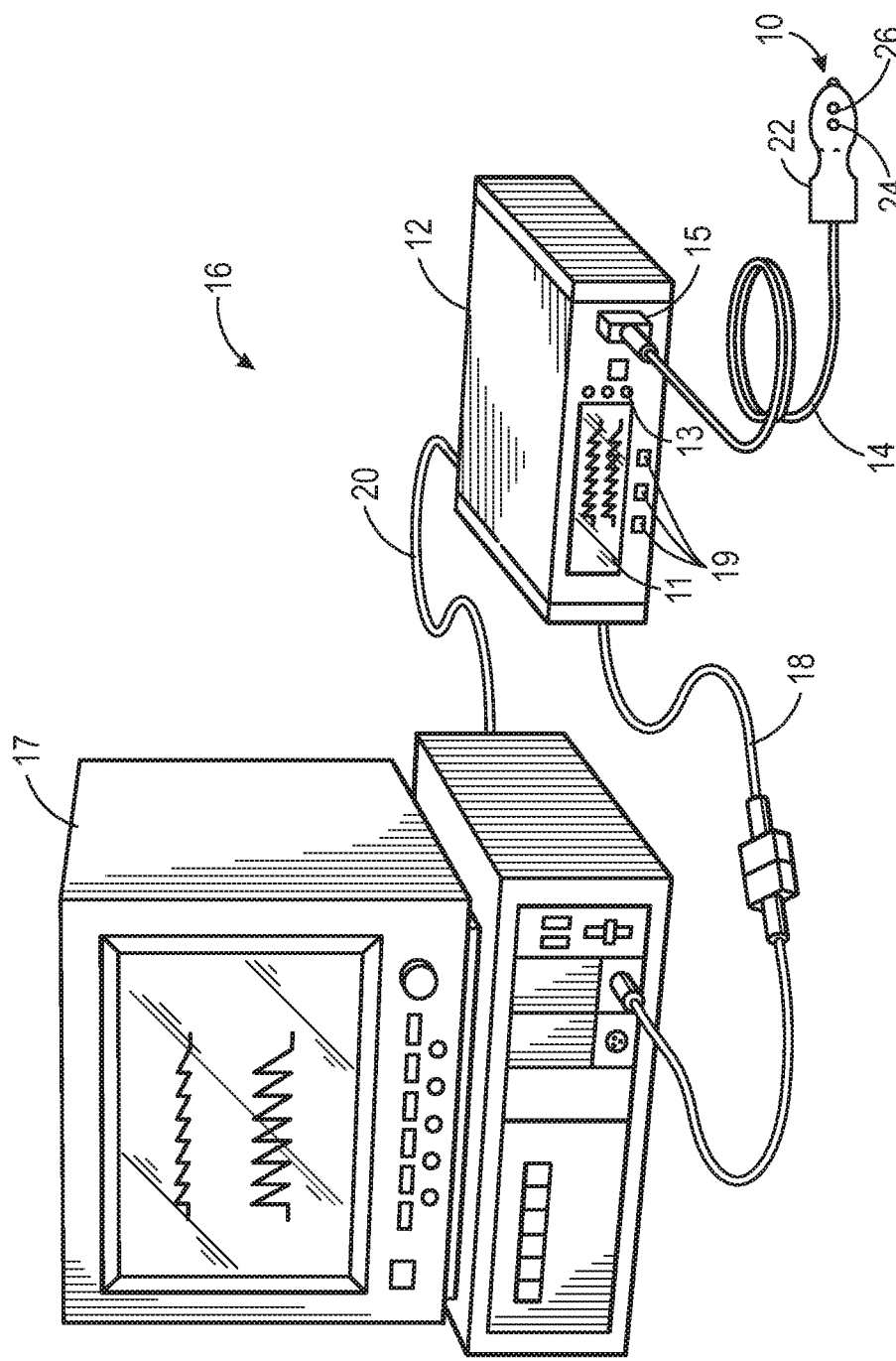
FIG. 1 illustrates a perspective view of a pulse oximeter in accordance with an embodiment.

FIG. 1 depicts a multi-configuration sensor 10 that may be used in conjunction with a monitor 12 in accordance with an embodiment of the present disclosure. The sensor 10 may be coupled to the monitor 12 via sensor cable 14 and sensor connector 15, or the sensor 10 may be coupled to a transmission device (not shown) to facilitate wireless transmission between the sensor 10 and the monitor 12. It should be noted that sensor cable 14 may be able to transmit a plurality of signals to the sensor 10 as well as transmit a plurality of signals from the sensor 10 to the monitor 12. The sensor 10 and the monitor 12 may generally be referred to as a pulse oximeter 16. Pulse oximeter 16 may be any suitable pulse oximeter, such as those available from Nellcor Puritan Bennett, LLC.

The monitor 12 of the pulse oximeter 16 may be configured to display calculated parameters on a display 11. As illustrated in FIG. 1, the display 11 may be integrated into the monitor 12 and may be configured to display computed physiological data including, for example, an oxygen saturation percentage, a pulse rate, and/or a plethysmographic waveform of a patient. As is known in the art, the oxygen saturation percentage may be a functional arterial hemoglobin oxygen saturation measurement in units of percentage $SpO_2$, while the pulse rate may indicate a patient's pulse rate in beats per minute. The monitor 12 may also display information related to alarms, monitor settings, and/or signal quality via indicator lights 13.

As described above, the monitor 12 may connect to an external sensor 10, via a cable 14 which connects to the monitor 12 via a sensor connector 15. The sensor 10 may be of a disposable or a non-disposable type. Furthermore, the sensor 10 may obtain readings from a patient that can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient.

Furthermore, to upgrade conventional operation provided by the monitor 12 (e.g., to provide additional functions), the monitor 12 may be coupled to a multi-parameter patient monitor 17 via a cable 18 connected to a sensor input port or via a cable 20 connected to a digital communication port, or through wireless transmission components (not shown). Alternatively, the monitor 12 may be integrated into the multi-parameter patient monitor 17. To facilitate user input, the monitor 12 may include a plurality of control inputs 19. The control inputs 19 may include fixed function keys, programmable function keys, and soft keys. Specifically, the control inputs 19 may correspond to soft key icons in the display 11. Pressing control inputs 19 associated with, or adjacent to, an icon in the display may select a corresponding option that may change the operation of, for example, the monitor 12 and/or the sensor 10. Alternatively, the multi-parameter patient monitor 17 may connect directly to the sensor 10 and may perform in a substantially similar manner to the monitor 12.

The sensor 10 may be a multiple configuration sensor capable of being applied to a multiple placement sites (e.g., multiple tissue sites such as a patient's finger, a patient's forehead, etc.). The sensor 10 may include a sensor body 22 that includes an emitter 24 and a detector 26 disposed on its surface. As depicted, the emitter 24 and detector 26 may be arranged in a reflectance-type configuration in which the emitter 24 and detector 26 are typically placed on the same side of the sensor site. Reflectance type sensors may operate by emitting light into the tissue and detecting the reflected light that is transmitted and scattered by the tissue. Reflectance type sensors detect light photons that are scattered back to the detector 26. The sensor 10 may also be configured as a transmittance type sensor whereby the emitter 24 and detector 26 are typically placed on differing sides of the sensor site. In this manner, the detector 26 may detect light that has passed through one side of a tissue site to an opposite side of the tissue site. Furthermore, the sensor 10 may include both reflectance and transmittance type arrangements, as further described below with respect to FIGS. 2 and 6.

Figure 2:
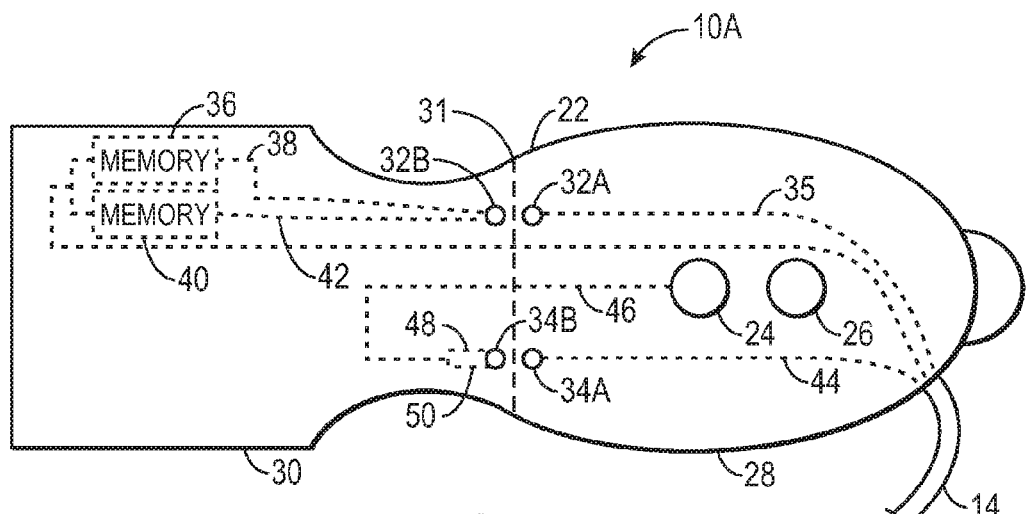
FIG. 2 illustrates an embodiment of the sensor of FIG. 1, in accordance with an embodiment.

Sensor 10 disclosed herein may have multiple possible configurations. FIG. 2 illustrates an exemplary bandage-type sensor 10A appropriate for use on multiple sites of a patient, for example, on a patient's digit 27 (see FIG. 3) or a patient's forehead 29 (see FIG. 4). The sensor body 22 includes an emitter 24 and a detector 26 disposed on a detector portion 28 of its surface. As depicted, the emitter 24 and detector 26 may be arranged in a reflectance-type configuration in which the emitter 24 and detector 26 are placed on the same side of the sensor site. Additionally, the sensor 10A may include a support portion 30 opposite from the detector portion 28 of the sensor body 22. In one embodiment, the sensor body 22 may be flexible about a radial axis 31, such that the detector portion 28 and the support portion 30 of the sensor 10A may be wrapped around, for example, a patient's digit 27, to achieve a substantially conforming and secure fit. That is, the support portion 30 provides additional surface area that allows the sensor body 22 to be able to wrap around a tissue site of a patient, which may provide a more secure fit for the sensor 10A. The sensor 10A may also include an adhesive layer (not shown) in order to enhance the sensor's fit to the tissue of a patient. As shown, the emitter 24 and the detector 26 may be arranged to be secured to, for example, the palmar side of the digit 27. Alternatively, the sensor 10A may be applied to, for example, a digit of a patient such that the emitter 24 and the detector 26 are secured to the nail side of the digit 27.

Figure 3:
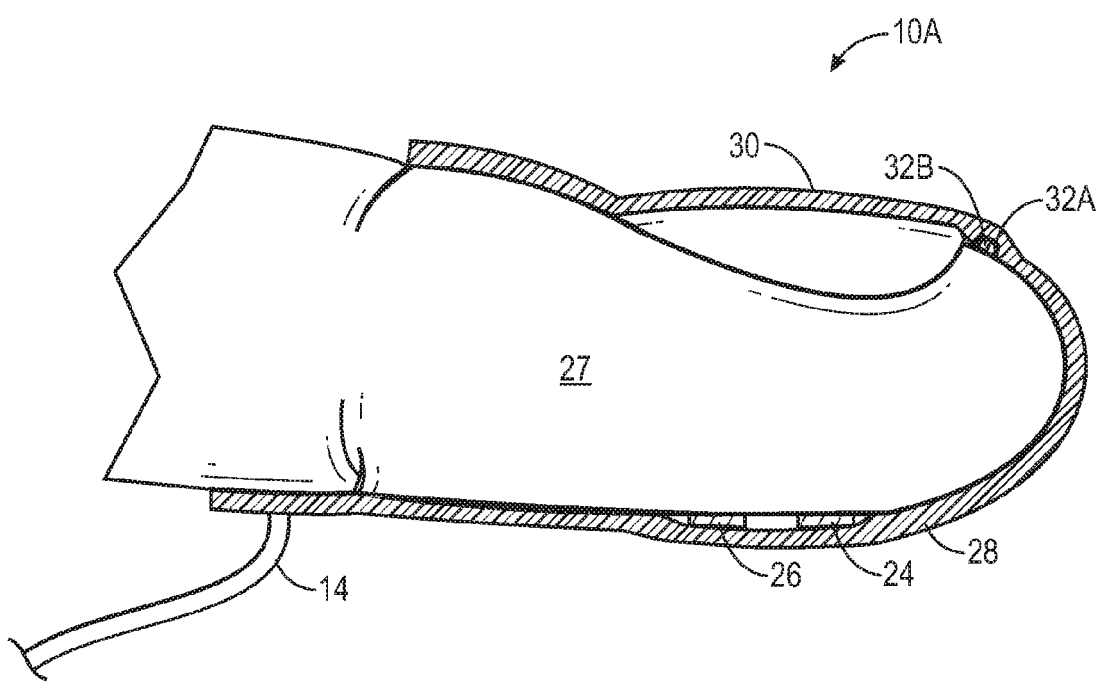
FIG. 3 illustrates the sensor of FIG. 1 in a first configuration, in accordance with an embodiment.
Figure 4:
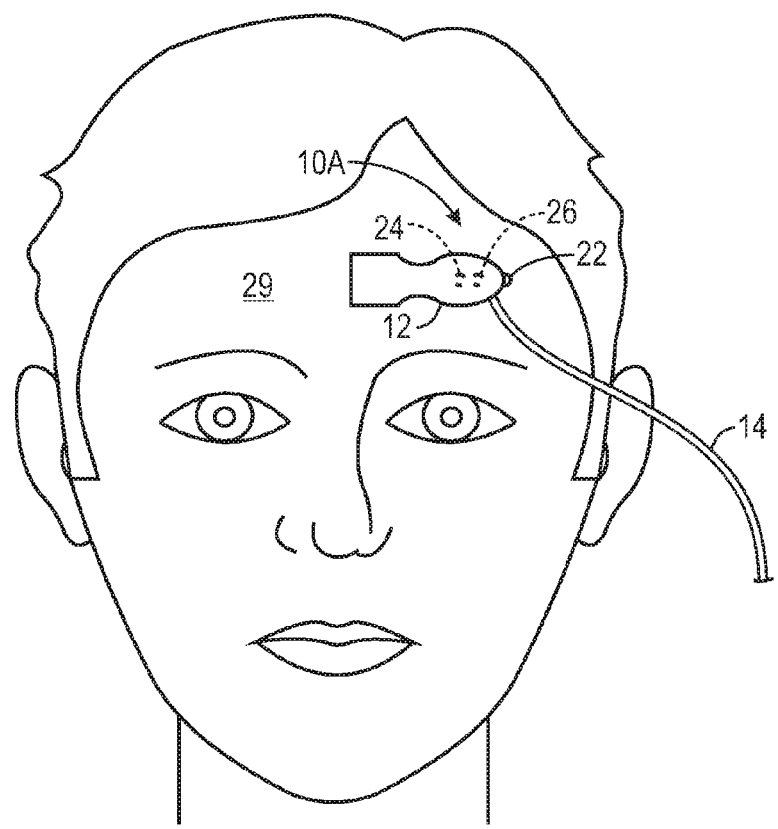
FIG. 4 illustrates the sensor of FIG. 1 in a second configuration, in accordance with an embodiment.

The sensor 10A may also include one or more sets of contacts 32A-B and 34A-B. As may be seen, contact 32A may be coupled to sensor cable 14 for receiving, for example, power, from the monitor 12 along conductive path 35. Contact 32B may be coupled to memory 36 along conductive path 38 and also may be coupled to memory 40 along conductive path 42. In operation, contact 32A and contact 32B may operate as a switch such that when the sensor 10A is in a curved position, such as seen in FIG. 3, conductive path 38 receives signals from conductive path 35. Furthermore, when the sensor 10A is in a straightened position, such as seen in FIG. 4, conductive path 42 receives signals from conductive path 35. In this manner, memory 36 may be activated when the sensor 10A is in a curved position and memory 40 may be activated when sensor 10A is in a straightened position. It should be noted that the sensor 10A may operate in the opposite manner as suggested above, that is, memory 36 may be activated when the sensor 10A is in a straightened position and memory 40 may be activated when sensor 10A is in a curved.

It should also be noted that while memory 36 and 40 are illustrated as housed in the sensor 10A, in other embodiments, memory 36 and/or memory 40 may be housed in the sensor connector 15. Additionally, resistors may be utilized in place of memory 36 and 40, whereby the resistors correspond to calibration coefficients (or calibration curves) stored in the monitor 12. That is, resistors that best fit calibration curves stored in the monitor 12 for a given sensor (e.g., 10A) at a given patient site (i.e. in a given configuration) may be utilized such that the resistor values correspond to the actual wavelengths transmitted by the a given emitter (e.g., 24) as well as coefficients used in algorithms for computing the physiological parameters of the patient at a given site. In this manner, the resistors and/or memory 36 and 40 may be sensor configuration devices.

Contacts 34A-B may operate in a manner similar to that described above with respect to contacts 32A-B. Contact 34A may be coupled to the monitor 12 via conductive path 44. Contact 34B may be coupled to emitter 24 along conductive path 46, which may include a convergence of conductive paths 48 and 50. In operation, contact 34A and contact 34B may operate as a switch such that when the sensor 10A is in a curved position, such as seen in FIG. 3, conductive path 48 receives signals from conductive path 44. Furthermore, when the sensor 10A is in a straightened position, such as seen in FIG. 4, conductive path 50 receives signals from conductive path 44. Furthermore, while the sensor 10A is transitioning between a curved and a straightened position (and vice versa) no signals are received across conducting path 46. The details of this process will be described below with respect to FIG. 5.

Figure 5:
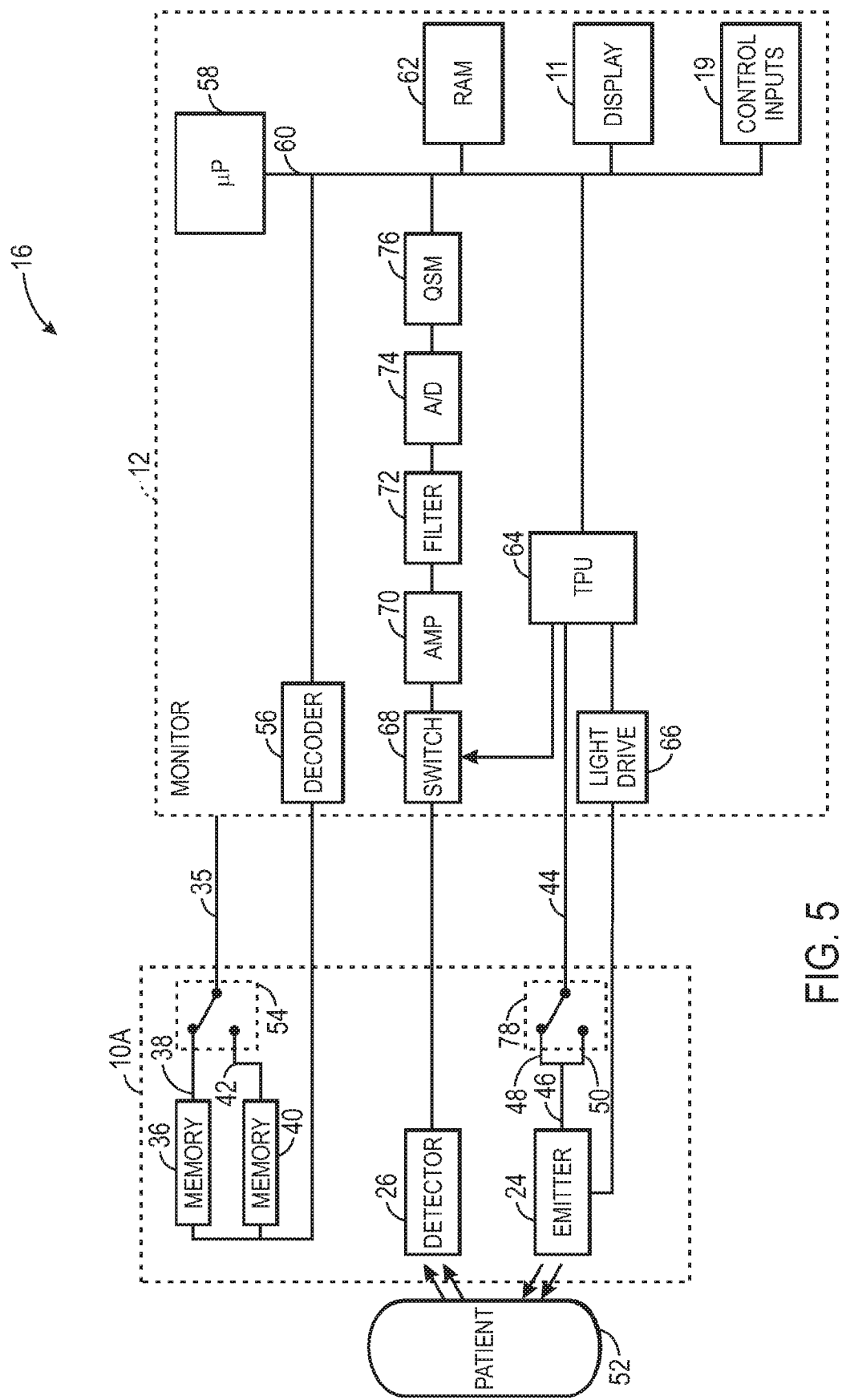
FIG. 5 illustrates a simplified block diagram of the pulse oximeter in FIG. 1, according to an embodiment.

Turning to FIG. 5, a simplified block diagram of a pulse oximeter 16 is illustrated in accordance with an embodiment. Specifically, certain components of the sensor 10A and the monitor 12 are illustrated in FIG. 5. The sensor 10A may include an emitter 24, a detector 26, memory 36, and memory 40. It should be noted that the emitter 24 may be capable of emitting at least two wavelengths of light, e.g., RED and infrared (IR) light, into the tissue of a patient 52 to calculate the patient's 52 physiological characteristics, where the RED wavelength may be between about 600 nanometers (nm) and about 700 nm, and the IR wavelength may be between about 780 nm and about 1000 nm. The emitter 24 may include a single emitting device, for example, with two light emitting diodes (LEDs) or the emitter 24 may include a plurality of emitting devices with, for example, multiple LED's at various locations. Regardless of the number of emitting devices, the emitter 24 may be used to measure, for example, water fractions, hematocrit, or other physiologic parameters of the patient 52. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure.

In one embodiment, the detector 26 may be an array of detector elements that may be capable of detecting light at various intensities and wavelengths. In operation, light enters the detector 26 after passing through the tissue of the patient 52. The detector 26 may convert the light at a given intensity, which may be directly related to the absorbance and/or reflectance of light in the tissue of the patient 52, into an electrical signal. That is, when more light at a certain wavelength is absorbed or reflected, less light of that wavelength is typically received from the tissue by the detector 26. After converting the received light to an electrical signal, the detector 26 may send the signal to the monitor 12, where physiological characteristics may be calculated based at least in part on the absorption of light in the tissue of the patient 52.

Additionally the sensor 10A may include memory 36 and 40, which may contain information about the sensor 10A, such as what type of sensor it is (e.g., whether the sensor is intended for placement on a forehead 29 or digit 27) and the wavelengths of light emitted by the emitter 24 or calibration coefficients. That is, memory 36 may include information relating to the sensor 10A when it is in, for example, a curved position (e.g., contacting a digit 27 of the patient 52) while memory 40 may include information relating to the sensor 10A when it is in, for example, a straightened position (e.g., contacting the forehead 29 of the patient 52). This information may allow the monitor 12 to select appropriate algorithms and/or calibration coefficients for calculating the patient's 52 physiological characteristics. The memory 36 and 40 may be erasable programmable read-only memory (EPROM) or may be another type of non-volatile memory that retains its data when regardless of whether power is supplied. Each of memory 36 and 40 may, for instance, store one or more of the following information for communication to the monitor 12: the type of the sensor 10A; the wavelengths of light emitted by the emitter 24; and the proper calibration coefficients and/or algorithms to be used for calculating the patient's 52 physiological characteristics.

As previously discussed with respect to FIG. 2, contacts 32A-B may form a switch. This switch is represented by switch 54 in FIG. 5. As may be seen, the switch 54 may allow for the activation of either memory 36 or memory 40. As previously described, this selection (i.e. the switching performed via the switch 54) may be dependent on whether the sensor 10A is in a straightened or in a curved position. Regardless of which memory 36 or 40 is selected via the switch 54, data from the selected memory, e.g., 36, may be transmitted to the decoder 56 for decoding. The decoder 56 may, for instance, decode the signals from the selected memory, e.g., 36, and may provide the decoded information to the processor 58. The decoded signals may provide information to the processor 58 such as the type of the sensor 10A and the wavelengths of light emitted by the emitter 24 so that proper calibration coefficients and/or algorithms to be used for calculating the patient's 52 physiological characteristics may be selected and utilized by the processor 58.

As described above, the monitor 12 may include processor(s) 58 that may include one or more microprocessors, such as one or more "general-purpose" microprocessors, one or more special-purpose microprocessors and/or ASICS, or some combination of such processing components. The processors 58 also may be connected to an internal bus 60. Also connected to the bus 60 may be a RAM memory 62 and the display 11. A time processing unit (TPU) 64 may provide timing control signals to light drive circuitry 66, which controls when the emitter 24 is activated, and if multiple light sources are used, the multiplexed timing for the different light sources. TPU 64 may also control the gating-in of signals from detector 26 through a switching circuit 68. These signals are sampled at the proper time, depending at least in part upon which of multiple light sources is activated, if multiple light sources are used. The received signal from the detector 26 may be passed through an amplifier 70, a low pass filter 72, and an analog-to-digital converter 74 for amplifying, filtering, and digitizing the electrical signals from the sensor BOA. The digital data may then be stored in a queued serial module (QSM) 76, for later downloading to RAM 62 as QSM 76 fills up. In an embodiment, there may be multiple parallel paths for separate amplifiers, filters, and A/D converters for multiple light wavelengths or spectra received.

The monitor 12 may also be able to determine if a sensor 10A is connected to the monitor 12 and may begin an initialization process when a sensor 10A is connected to the monitor. For example, when a sensor 10A is first connected to the monitor 12, the monitor may determine certain characteristics of the sensor 10A. For example, the monitor 12 may determine the manufacturer of the sensor 10A to determine compatibility, the type of sensor 11A (e.g., transmittance type, reflectance type, flat, curved, etc.), the wavelengths of light emitted by the emitter 24, etc. It should be noted that these characteristics may be read from an activated memory, e.g. 36. Once the sensor 10A is determined to be compatible, and the sensor 10A characteristics are identified, the monitor 12 may begin to operate in the manner described above with respect to FIG. 5. Furthermore, if a sensor 10A is unplugged from the monitor 12, the monitor may cease operation. Upon a sensor 10A being plugged into the monitor 12 again, the initialization process described above may begin anew.

In one embodiment, the TPU 64 may be connected to the emitter 24 via conducting line 44 and switch 78. Switch 78 may be representative of contacts 34A-B of FIG. 2. As may be seen, switch 78 may couple either conductive path 48 to conductive path 44 or conductive path 50 to conductive path 44. As previously discussed, this selection (i.e. the switching performed via the switch 78) may be dependent on whether the sensor 10A is in a straightened or in a curved position. However, as the sensor 10A is moved from a straightened position to a curved position (or vice versa), there is a period of time in which the switch 78 is switching between conductive lines 48 and 50. During this time, no connection between the conductive line 44 and the emitter 24 exists. Accordingly, during this time the monitor 12 may operate as if a sensor 10A is not connected to the monitor 12. That is, the monitor 12 will cease to transmit signals to the sensor 10A until a sensor is recognized as attached to the monitor 12 once again (i.e., until switch 78 has completed switching). This recognition of a sensor 10A being attached to the monitor 12 may begin the initialization process described above.

This initialization process may include reading information from the activated memory, e.g., 36 if the sensor 10A is curved and 40 if the sensor 10A is straightened. In this manner, if the sensor 10A is initially in a curved configuration, the monitor 12 receives proper calibration coefficients and/or algorithms from memory 36 corresponding to a curved configuration of the sensor 10A for use in calculating the patient's 52 physiological characteristics. Furthermore, if the sensor 10A is then straightened, switch 78 will cause the monitor 12 to sense a lack of a sensor 10A and the monitor 12 will attempt to perform the initialization process with the sensor 10A once switch 78 is connected to conducting line 50. The straightening of the sensor 10A will have also caused the switch 54 to switch to allow line 42 to be coupled to conductive line 35, thus activating memory 40. Thus, monitor 12 accesses active memory 40 from which the monitor 12 receives proper calibration coefficients and/or algorithms corresponding to the straightened configuration of the sensor 10A. These coefficients may then be utilized calculating the patient's 52 physiological characteristics. Accordingly, proper coefficients relating to either a straightened or a curved configuration of the sensor 10A may be transmitted to the monitor 12 without any input from a user separate from shaping the sensor 10A into a desired configuration.

Figure 6:
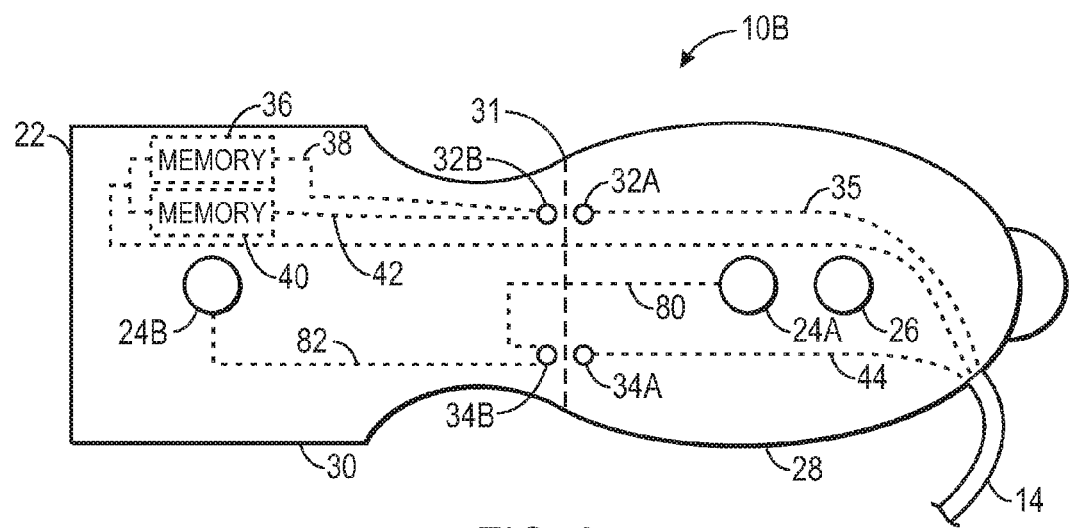
FIG. 6 illustrates an second embodiment of the sensor of FIG. 1, in accordance with an embodiment.

FIG. 6 illustrates a second sensor 10B that may be similar to sensor 10A. For example, similar to sensor 10A, sensor 10B may be a bandage-type sensor appropriate for use on multiple sites of a patient, for example, on a patient's 52 digit 27 (see FIG. 3) or a patient's 52 forehead 29 (see FIG. 4). However, unlike sensor 10A, illustrated sensor 10B includes both a reflectance type emitter 24A and a transmittance type emitter 24B. The reflectance type emitter 24A and a detector 26 may be disposed on a detector portion 28 of its surface while the transmittance type emitter 24B may be disposed on the support portion 30 opposite from the detector portion 28 of the sensor body 22. In one embodiment, the sensor body 22 may be flexible about a radial axis 31, such that the detector portion 28 and the support portion 30 of the sensor 10B may be wrapped around, for example, a patients 52 digit 27, to achieve a substantially conforming and secure fit. Furthermore, the sensor 10B may also include an adhesive layer (not shown) in order to enhance the sensor's fit to the tissue of a patient 52.

The sensor 10B may also include one or more sets of contacts 32A-B and 34A-B. As may be seen, contact 32A may be coupled to sensor cable 14 for receiving, for example, power, from the monitor 12 along conductive path 35. Contact 32B may be coupled to memory 36 along conductive path 38 and also may be coupled to memory 40 along conductive path 42. In operation, contact 32A and contact 32B may operate as a switch such that when the sensor 10B is in a straightened position, such as seen in FIG. 4, conductive path 38 receives signals from conductive path 35. Furthermore, when the sensor 10B is in a curved position, such as seen in FIG. 3, conductive path 42 receives signals from conductive path 35. In this manner, memory 36 may be activated when the sensor 10A is in a straightened position and memory 40 may be activated when sensor 10A is in a curved position.

Contacts 34A-B may operate in a manner similar to that described above with respect to contacts 32A-B. Accordingly, contact 34A may be coupled to the monitor 12 via conductive path 44 while contact 34B may be coupled to emitter 24A along conductive path 80 and emitter 24B along conductive path 82. In operation, contact 34A and contact 34B may operate as a switch such that when the sensor 10A is in a straightened position, such as seen in FIG. 4, conductive path 80 receives signals from conductive path 44. Furthermore, when the sensor 10A is in a curved position, such as seen in FIG. 3, conductive path 82 receives signals from conductive path 44. Furthermore, while the sensor 10A is transitioning between a curved and a straightened position (and vice versa) no signals are received across either of conducting paths 80 or 82. The details of this process will be described below with respect to FIG. 7.

Figure 7:
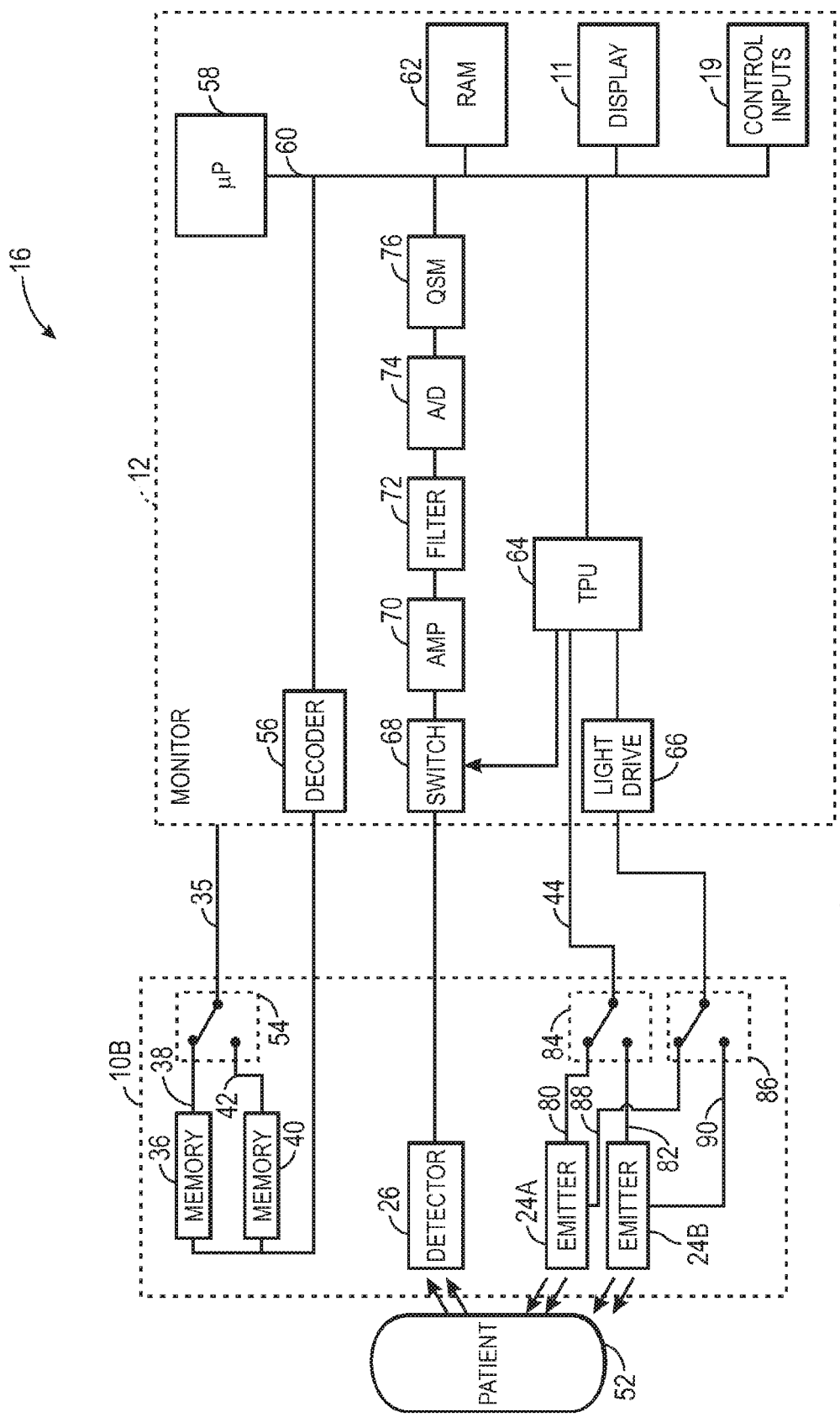
FIG. 7 illustrates a simplified block diagram of the pulse oximeter in FIG. 1 in conjunction with the sensor of FIG. 6, in accordance with an embodiment.

Turning to FIG. 7, a simplified block diagram of a pulse oximeter 16 is illustrated in accordance with an embodiment. Specifically, certain components of the sensor 10B and the monitor 12 are illustrated in FIG. 7. The sensor 10B may include the two emitters 24A-B described above, a detector 26, memory 36, and memory 40. It should be noted that each of the emitters 24A-B may be capable of emitting at least two wavelengths of light, e.g., RED and infrared (IR) light, into the tissue of a patient 52 to calculate the patient's 52 physiological characteristics, where the RED wavelength may be between about 600 nanometers (nm) and about 700 nm, and the IR wavelength may be between about 780 nm and about 1000 nm. The emitters 24A-B may include a single emitting device, for example, with two light emitting diodes (LEDs) or the emitters 24A-B may include a plurality of emitting devices with, for example, multiple LED's at various locations. Regardless of the number of emitting devices, the emitter 24 may be used to measure, for example, water fractions, hematocrit, or other physiologic parameters of the patient 52. Furthermore, emitter 24A may be used as a reflectance type emitter while emitter 24B may be used as a transmittance type emitter, as described above.

In one embodiment, the detector 26 may be an array of detector elements that may be capable of detecting light at various intensities and wavelengths. In operation, light enters the detector 26 after passing through the tissue of the patient 52. The detector 26 may convert the light at a given intensity, which may be directly related to the absorbance and/or reflectance of light in the tissue of the patient 52, into an electrical signal. That is, when more light at a certain wavelength is absorbed or reflected, less light of that wavelength is typically received from the tissue by the detector 26. After converting the received light to an electrical signal, the detector 26 may send the signal to the monitor 12, where physiological characteristics may be calculated based at least in part on the absorption of light in the tissue of the patient 52.

Additionally the sensor 10A may include memory 36 and 40, which may contain information about the sensor 10A, such as what type of sensor it is (e.g., whether the sensor is intended for placement on a forehead or digit) and the wavelengths of light emitted by the emitter 24. That is, memory 36 may include information relating to the sensor 10A when it is in, for example, a straightened position (e.g., contacting the forehead 29 of the patient 52) while memory 40 may include information relating to the sensor 10A when it is in, for example, a curved position (e.g., contacting a digit 27 of the patient 52). This information may allow the monitor 12 to select appropriate algorithms and/or calibration coefficients for calculating the patient's 52 physiological characteristics.

As previously discussed with respect to FIG. 6, contacts 32A-B may form a switch. This switch is represented by switch 54 in FIG. 7. As may be seen, the switch 54 may allow for the activation of either memory 36 or memory 40. As previously described, this selection (i.e. the switching performed via the switch 54) may be dependent on whether the sensor 10A is in a straightened or in a curved position. Regardless of which memory 36 or 40 is selected via the switch 54, data from the selected memory, e.g., 36, may be transmitted to the decoder 56 for decoding. The decoded signals may provide information to the processor 58 such as the type of the sensor 10A and the wavelengths of light emitted by the emitter 24 so that proper calibration coefficients and/or algorithms to be used for calculating the patient's 52 physiological characteristics may be selected and utilized by the processor 58

The monitor 12 may include substantially similar components to those described above with respect to FIG. 5. Accordingly, the monitor 12 may be able to determine if a sensor 10B is connected to the monitor 12 and may begin an initialization process when a sensor 10B is connected to the monitor. For example, when a sensor 10B is first connected to the monitor 12, the monitor may determine certain characteristics of the sensor 10B. For example, the monitor 12 may determine the manufacturer of the sensor 10B to determine compatibility, the type of sensor 10B (e.g., transmittance type, reflectance type, flat, curved, etc.), the wavelengths of light emitted by the emitter 24, etc. It should be noted that these characteristics may be read from an activated memory, e.g. 36. Once the sensor 10B is determined to be compatible, and the sensor 10B characteristics are identified, the monitor 12 may begin to operate in the manner described above with respect to FIG. 2. Furthermore, if a sensor 10B is unplugged from the monitor 12, the monitor may cease operation. Upon a sensor 10B being plugged into the monitor 12 again, the initialization process described above may begin anew.

In one embodiment, the TPU 64 may be connected to emitters 24A-B via conducting line 44 and switch 84. Switch 84 may be representative of contacts 34A-B of FIG. 2. As may be seen, switch 84 may couple either conductive path 80 to conductive path 44 or conductive path 82 to conductive path 44. As previously discussed, this selection (i.e. the switching performed via the switch 84) may be dependent on whether the sensor 10B is in a straightened or in a curved position. However, as the sensor 10B is moved from a straightened position to a curved position (or vice versa), there is a period of time in which the switch 84 is switching between conductive lines 80 and 82. During this time, no connection between the conductive line 44 and either emitter 24A or 24B exists. Accordingly, during this time the monitor 12 may operate as if a sensor 10B is not connected to the monitor 12. That is, the monitor 12 will cease to transmit signals to the sensor 10B until a sensor is recognized as attached to the monitor 12 once again (i.e., until switch 84 has completed switching). This recognition of a sensor 10B being attached to the monitor 12 may begin the initialization process described above.

This initialization process may include reading information from the activated memory, e.g., 36 if the sensor 10B is straightened and 40 if the sensor 10B is curved. In this manner, if the sensor 10B is initially in a straightened configuration, the monitor 12 receives proper calibration coefficients and/or algorithms from memory 36 corresponding to a curved configuration of the sensor 10B for use in calculating the patient's 52 physiological characteristics. Furthermore, if the sensor 10B is then curved, switch 84 will cause the monitor 12 to sense a lack of a sensor 10B and the monitor 12 will attempt to perform the initialization process with the sensor 10B once switch 84 is connected to conducting line 82. The curving of the sensor 10B will have also caused the switch 54 to switch to allow line 42 to be coupled to conductive line 35, thus activating memory 40. Thus, monitor 12 accesses active memory 40 from which the monitor 12 receives proper calibration coefficients and/or algorithms corresponding to the curved configuration of the sensor 10B. These coefficients may then be utilized calculating the patient's 52 physiological characteristics. Accordingly, proper coefficients relating to either a straightened or a curved configuration of the sensor 10A may be transmitted to the monitor 12 without any input from a user separate from shaping the sensor 10A into a desired configuration.

Similar to switch 84, switch 86 may also be located in contacts 34A-B. Accordingly, the curving of the sensor 10B may also cause the switch 86 to switch from activating conductive line 88 to activating conductive line 90, causing the light drive circuitry 66, which controls when the emitters 24A-B are activated, to cease to activate emitter 24A and instead, activate emitter 24B. In this manner, the act of manipulating the sensor 10B into a curved or a straightened position may allow for a transmittance or reflectance type emitter to automatically be selected for use. Furthermore, the monitor 12 may be able to automatically determine which type of emitter 24A-B is being activated based on the configuration of the sensor 10B.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, factional hemoglobin, intravascular dyes, and/or water content. Rather, the various embodiments may cover all modifications, equivalents, and alternatives falling within the spirit and scope of the disclosure as defined by the following appended claims.

What is claimed is:

1. A system, comprising:
   a monitor;
   a sensor configured to be coupled to the monitor, the sensor comprising:
   a sensor body configured to flex between a first configuration in which the sensor body is disposed in a substantially flat position and adapted to be applied to a first tissue site and a second configuration in which the sensor body is disposed in a flexed position and adapted to be applied to a second tissue site, wherein the sensor is configured to measure a physiological characteristic;
   a first memory device storing a first set of calibration data; and a second memory device storing a second set of calibration data, wherein the first memory device is accessible by the monitor in the first configuration and the second memory device is accessible by the monitor in the second configuration.

2. The system of claim 1, wherein the monitor comprises a pulse oximetry monitor.

3. The system of claim 1, wherein the sensor comprises a sensor connector.

4. The system of claim 3, wherein the sensor connector is configured to house the first memory and the second memory.

5. The system of claim 3, wherein the sensor body is configured to house the first memory and the second memory.

6. The system of claim 1, wherein the sensor comprises a first switch configured to allow activation of the first memory device in the first configuration and activation of the second memory device in the second configuration.

7. The system of claim 6, wherein the sensor comprises a first emitter configured to transmit light in the first configuration and a second emitter configured to transmit light in the second configuration.

8. The system of claim 7, wherein the sensor comprises a second switch configured to allow activation of the first emitter in the first configuration and activation of the second emitter in the second configuration.

9. The system of claim 8, wherein the sensor comprises a third switch configured to allow sensing of the first emitter in the first configuration and sensing of the second emitter in the second configuration.

10. A medical sensor, comprising:
a sensor body comprising:
    a first sensor configuration device configured to store a first set of sensor parameters;
    a second sensor configuration device configured to store a second set of sensor parameters; and
    a first conductive path coupled to the first sensor configuration device and a second conductive path coupled to the second sensor configuration device, wherein the first conductive path is configured to be electrically connected to a third conductive path in a first configuration of the sensor and the second conductive path is configured to be electrically connected to the third conductive path in a second configuration of the sensor.

11. The sensor of claim 10, comprising a first switch configured to connect the first conductive path coupled to the first sensor configuration device in the first configuration and the second conductive path coupled to the second sensor configuration device in the second configuration to the third conductive path.

12. The sensor of claim 11, wherein the first switch comprises a first set of contacts, wherein the first switch switches between the first conductive path coupled to the first sensor configuration device and the second conductive path coupled to the second sensor configuration device based on contact between the first set of contacts in the first and second configurations.

13. The sensor of claim 11, comprising a first emitter, a second emitter, and a second switch configured to switch between each of the first and second emitters in the first configuration and in the second configuration, respectively.

14. The sensor of claim 13, wherein the second switch comprises a set of contacts, wherein the switch switches between the first emitter and the second emitter based on contact between the second set of contacts in the first and second configurations.

15. The sensor of claim 10, comprising an emitter coupled to a first and a second conductive line, and a switch configured to switch between each of the two conductive lines in the first configuration and in the second configuration.

16. The sensor of claim 10, wherein the first sensor configuration device and second sensor configuration device are connected in parallel.

17. A system, comprising:
a flexible sensor body configured to flex between a first configuration in which the sensor body is disposed in a substantially flat position and a second configuration in which the sensor body is disposed in a flexed position, wherein the sensor is configured to measure a physiological characteristic;
a first memory device configured to store a first set of calibration data;
a second memory device configured to store a second set of calibration data; and
a monitor coupled to the sensor, wherein the first memory device is accessible by the monitor when the sensor is in the first configuration and the second memory device is accessible by the monitor in the second configuration.

18. The system of claim 17, comprising a switch configured to electrically connect the first memory device in the first configuration in a first position to the monitor and to electrically connect the second memory device in the second configuration to the monitor in a second position.

19. The system of claim 18, wherein the monitor is configured to undertake an initialization process when the switch switches from the first position to the second position, wherein the initialization process comprises accessing the electrically connected first or second memory.

20. The system of claim 19, wherein the monitor is configured to calculate the physiological characteristic based data accessed from the electrically connected first or second memory.

* * * * *